(12) United States Patent
Hochman et al.

(10) Patent No.: US 7,771,199 B2
(45) Date of Patent: Aug. 10, 2010

(54) BONE CUTTING OSTEOTOME TOOL AND METHOD FOR PREPARING A SURGICAL SINUS-LIFT OSTEOTOMY

(75) Inventors: Mark N. Hochman, Great Neck, NY (US); Emmanuel G. Sotirakis, Athens (GR); Alan R. Balfour, Petaluma, CA (US); Joseph Edward Carchidi, West Bridgewater, MA (US)

(73) Assignee: ACE Surgical Supply Co, Inc., Brockton, MA (US)

( * ) Notice: Subject to any disclaimer, the term of this patent is extended or adjusted under 35 U.S.C. 154(b) by 0 days.

(21) Appl. No.: 11/250,107

(22) Filed: Oct. 13, 2005
(Under 37 CFR 1.47)

(65) Prior Publication Data
US 2006/0172255 A1  Aug. 3, 2006

Related U.S. Application Data

(60) Provisional application No. 60/619,542, filed on Oct. 15, 2004.

(51) Int. Cl.
*A61C 5/00* (2006.01)
(52) U.S. Cl. ........................ 433/215; 433/144
(58) Field of Classification Search ......... 433/173–174, 433/165, 166, 215, 82, 144, 147; 606/170, 606/180, 80, 84; 408/59; 173/78, 80, 199
See application file for complete search history.

(56) References Cited

U.S. PATENT DOCUMENTS

| | | | | |
|---|---|---|---|---|
| 4,219,620 A | * | 8/1980 | Carse | 433/225 |
| 4,881,431 A | * | 11/1989 | Bieneck | 76/108.6 |
| 5,261,818 A | * | 11/1993 | Shaw | 433/165 |
| 5,429,504 A | * | 7/1995 | Peltier et al. | 433/165 |
| 5,711,315 A | * | 1/1998 | Jerusalmy | 128/898 |
| 5,989,025 A | * | 11/1999 | Conley | 433/76 |
| 7,125,253 B2 | * | 10/2006 | Kitamura et al. | 433/173 |
| 2001/0036616 A1 | * | 11/2001 | Swan | 433/88 |
| 2002/0150862 A1 | * | 10/2002 | Day | 433/173 |
| 2002/0177102 A1 | * | 11/2002 | Martin et al. | 433/173 |
| 2003/0026666 A1 | * | 2/2003 | Toublanc | 408/59 |

(Continued)

OTHER PUBLICATIONS

ACE Dental Implant System Catalog; ACE Sinus Lift Osteotomes, p. 173, printed 1999, USA ACE Surgical Supply Co., Inc.

(Continued)

*Primary Examiner*—Cris L Rodriguez
*Assistant Examiner*—Sunil K Singh
(74) *Attorney, Agent, or Firm*—John A. Haug

(57) ABSTRACT

A surgical tool for preparing a surgical sinus-lift osteotomy has a defined thread geometry in series with an osteotome tip to cut, crack and push bone from the sinus floor upward into the sinus cavity in a tactual, gentle and controlled motion. The apical osteotome tip is driven into a pre-drilled pilot osteotomy after the cutting threads are engaged and rotated until the sinus floor is cracked free. Once the bony sinus floor is cracked free, a fluid passageway can be pressurized with a sterile fluid at a defined pressure to release and push the sinus membrane upward into the sinus cavity to create a desired apical cavity for grafting while minimizing the risk of compromising or tearing the sinus membrane.

2 Claims, 1 Drawing Sheet

U.S. PATENT DOCUMENTS

2003/0105469 A1* 6/2003 Karmon .................. 606/92
2003/0175656 A1* 9/2003 Livne et al. .............. 433/201.1
2004/0064928 A1* 4/2004 Norwood ................ 29/222
2006/0084034 A1* 4/2006 Hochman ............... 433/173
2006/0121415 A1* 6/2006 Anitua Aldecoa ........... 433/165

OTHER PUBLICATIONS

U.S. Appl. No. 60/619,542, filed Oct. 15, 2004, Mark N. Hochman.

* cited by examiner

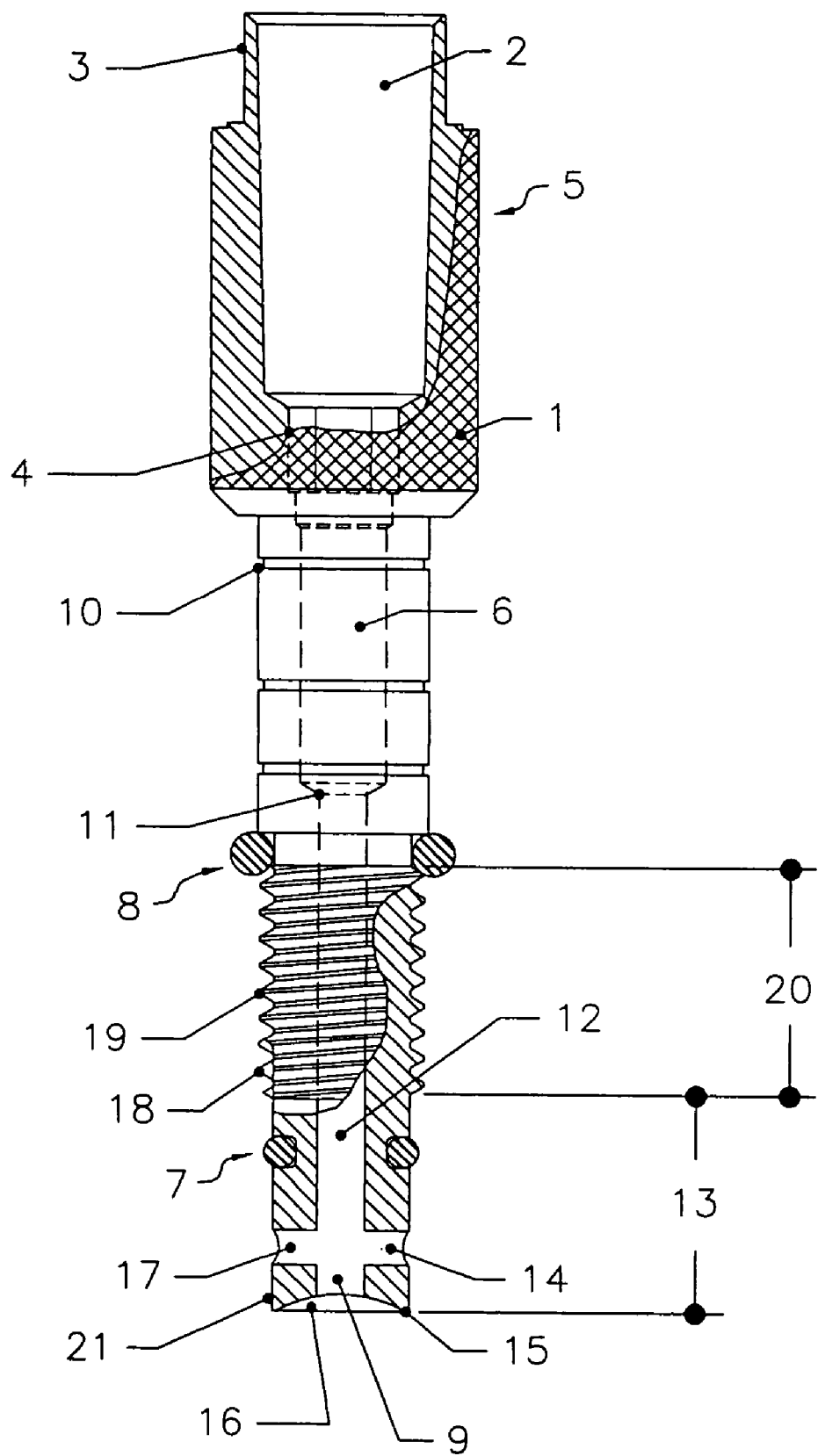

BONE CUTTING OSTEOTOME TOOL AND METHOD FOR PREPARING A SURGICAL SINUS-LIFT OSTEOTOMY

RELATED APPLICATIONS

Priority is claimed under 35 U.S.C. Section 119 (e)(1) of Provisional Application No. 60/619,542, filed Oct. 15, 2004.

FIELD OF THE INVENTION

This invention relates generally to surgical tools and more particularly to such tools and methods used for preparing an osteotomy with a sinus lift membrane procedure that allows for grafting and the insertion of a threaded form dental implant.

BACKGROUND OF THE INVENTION

The present invention addresses problems associated with preparing an osteotomy to receive a root formed dental implant in the area of the sinus floor. Presently, the technique for creating the vertical area for a root formed dental implant when insufficient bone is available is to use a sinus lifting procedure and graft the area of the newly formed cavity under the sinus membrane. Although several techniques are used to perform the membrane lifting procedure, the use of presently available tools risks the chance of tearing the membrane during the osteotomy preparation, or does not allow for the easy displacement of the membrane to form a suitable apical cavity. One such technique makes use of sinus lift osteotome cutting tools to create the desired cylindrical osteotomy and cavity space, however, these tools lack the tactile sensitivity needed for cracking the sinus floor with minimized risk of tearing the sinus membrane. Another surgical technique to create this desired space is to cut out a buccal window in the sinus area and gently push the membrane upward and outward to form an apical cavity. Although this technique is very successful if done correctly, the procedure requires a significant number of surgical steps and advanced surgical skills to prevent tearing of the membrane.

SUMMARY OF THE INVENTION

An object of the present invention is the provision of a method and apparatus for surgically preparing sinus-lift osteotomies while minimizing risks of damaging the sinus membrane tissue and allowing for the insertion of desired bone graft material and a dental implant fixture.

Another object of the invention is the provision of a surgical tool that can tactually cut, crack and push the sinus floor bone upwardly in a controlled motion until the sinus floor can be cracked free.

A further object of the invention is the provision of a tool having a fluid communication passageway to allow for a sterile fluid to be pumped into the tool at a defined pressure and allow for the sinus membrane to be displaced without compromising or tearing the membrane.

Yet another object of the invention is the provision of a tool which can be driven into a pre-drilled pilot osteotomy by hand with a ratchet or by using a surgical drilling unit.

Briefly stated, to overcome these limitations, a simple surgical tool is provided in accordance with a preferred embodiment of the invention that can be inserted, like a bone tap, into a pre-formed pilot osteotomy in the maxillary bone and threaded in an upward direction toward the sinus floor. As the tool is driven into the osteotomy towards the sinus floor, the tool's osteotome cutting tip cuts, cracks and pushes the sinus floor bone in an upwards direction. Since the insertion into the bone is achieved by rotating the distal cutting threads on the tool during insertion, the cracking of the sinus floor with the osteotome tip is done with a very tactual, gentle and controlled motion until the sinus floor cracks free. Once the bony sinus floor is cracked free, a sterile fluid can be administered through the center of the tool with a defined positive pressure in order to gently push the sinus membrane in an upward direction and create a newly formed cavity space. Once the desired cavity space is achieved, the tool can be easily removed and replaced with desired bone graft material and a dental implant fixture to complete the desired surgical augmentation.

Other objects and advantages of the present invention will be apparent from the following description.

BRIEF DESCRIPTION OF THE DRAWINGS

For a more complete understanding of the present invention and further advantages thereof, reference is now made to the following detailed description of the preferred embodiment taken in conjunction with the drawing in which:

the sole FIGURE is an elevational view, partly in cross section, of a threaded osteotome bone cutting tool made in accordance with the invention.

DETAILED DESCRIPTION OF THE PREFERRED EMBODIMENT

As shown in the sole figure of the drawing, a helically threaded osteotome bone cutting tool 5 made in accordance with the preferred embodiment of the invention comprises a generally elongated body having opposite coronal and apical ends and a longitudinal axis therebetween. A threaded shaft axial length portion 20 is serially formed with a cutting and driving axial length portion 13. The apical end face is defined by a generally cylindrical side wall and formed with a concave peripheral bevel 16 to provide a sharp cutting edge 15 that serves as a driving tip 21. This structure allows the driving tip to cut, crack and push the bone from the sinus floor in an upward direction into the sinus cavity. The threaded shaft axial length portion 20 incorporates a defined thread 19 with an apical cutting flute 18 that allows the tool to be rotated and driven into a pre-drilled pilot osteotomy with a tactual, gentle and controlled motion to assist in the action of cracking free of the sinus floor bone. Centrally located in tool 5 is a longitudinally extending opening 6 that reduces in cross sectional area at 11 to a fluid irrigation passageway or hole 12 for passage if sterile fluid. When sterile fluid is applied to the tool by locking a fluid dispenser onto the female Luer-lock connection 2 on tool 5, fluid is able to pass through opening 6 and passageway 12 of the tool and gently move the attached sinus membrane in an upward direction into the sinus cavity using a defined fluid pressure. This central irrigation passage hole 12 allows fluid to flow through an opening 9 in the apical end face and preferably also through two radially extending, or generally 90 degree holes 14 and 17, respectively, on the shaft of osteotome tip 13. To ensure maintenance of desired fluid pressure for lifting the sinus membrane, tool 5 incorporates two sealing O-rings, 7 and 8 respectively, on either axial side of threaded shaft axial length portion 20.

Coronal to the threaded shaft axial length portion 20 are a selected number of spaced apart, annular scored marks 10 that allow the user, i.e., the surgeon, to have a visual reference for the patient's tissue depths.

The coronal end of tool 5 incorporates a male polygonal driver head 3 that can be driven by a matching female hand driver ratchet (not shown). In addition to the female Luer-lock connection 2, tool 5 also incorporates a female polygonal driver surface 4 disposed apically of connection 2 that can be driven with a male manual (not shown) or contra-angle driver tool (not shown). Tool 5 also preferably includes an outer knurled shaft 1 that allows the user to tactually rotate the tool by hand.

Thus when used, the osteotome tip cuts, cracks and pushes the bone from the sinus floor upwardly toward the sinus cavity in a tactual, gentle and controlled motion when the tool is rotated during insertion using the distal cutting threads. The longitudinally extending passageway allows fluid to pass through the center of the tool and gently move the attached sinus membrane upwardly into the sinus cavity using a defined positive fluid pressure enabled by the two sealing O-rings (7, 8) without compromising or tearing the membrane tissue. Once the sinus membrane has been moved, the user can simply remove the positive fluid pressure from the tool and the fluid will be expressed from the newly formed cavity. The tool can then be unscrewed from the prepared osteotomy and a bony graft material can be inserted into the newly formed space. Additionally, due to the selected cutting thread design of the tool, once the tool is removed it can easily be replaced with a standard thread formed dental implant fixture.

Although the invention has been described with regards to a specific preferred embodiment thereof, variations and modifications will become apparent to those of ordinary skill in the art. It is therefore the intent that the appended claims be interpreted as broadly as possible in view of the prior art to include all such variations and modifications.

What is claimed:

1. A method for preparing a surgical sinus-lift osteotomy comprising the steps of:
   forming a cylindrical pilot hole having a diameter and a longitudinal axis in the maxillary bone in alignment with the sinus floor,
   taking a tool having a continuous sharp circular cutting edge having a diameter the same as the diameter of the pilot hole and having an axially extending opening and placing said circular cutting edge in the pilot hole in an orientation so that the circular cutting edge lies in a plane perpendicular to the longitudinal axis,
   while maintaining said orientation, moving the circular cutting edge in a helical motion toward and into engagement with the sinus floor until the sinus floor is cut and cracked, and,
   while maintaining the circular cutting edge within the pilot hole, delivering sterile fluid through the said axially extending opening at a selected pressure and maintaining the delivered fluid at the selected pressure to release and push the sinus membrane into the sinus cavity.

2. A method according to claim 1 further comprising the step of moving the circular cutting edge by use of a bone thread.

* * * * *